United States Patent [19]

Kent

[11] Patent Number: 4,838,886
[45] Date of Patent: Jun. 13, 1989

[54] PAD HOLDER

[76] Inventor: Gail H. Kent, 3 Redfern St., Asheville, N.C. 28806

[21] Appl. No.: 23,420

[22] Filed: Mar. 9, 1987

[51] Int. Cl.⁴ .................. A61F 13/16; A41B 9/00; A41D 1/14
[52] U.S. Cl. .................. 604/392; 604/393; 604/396; 2/111; 2/221
[58] Field of Search .............. 604/386, 387, 391, 392, 604/390, 393, 395–402; 2/237, 235, 236, 323, 338, 325, 220, 221, 400, 402, 406, 111, 221, 319, 337; 128/447, 518 B, 558, 518 R, 561, 562; 24/581, 577, 576; D2/2, 3, 5, 6, 39; D11/212; D30/24; 450/41, 87, 134, 137, 138

[56] References Cited

U.S. PATENT DOCUMENTS

| Re. 28,483 | 7/1975 | Ralph | 604/397 |
|---|---|---|---|
| 971,659 | 10/1910 | Bewsic | 2/402 |
| 1,079,479 | 11/1913 | Earnshaw | 604/392 |
| 1,977,604 | 10/1934 | Alsop | 604/394 |
| 2,294,617 | 9/1942 | Horowitz | 604/386 |
| 2,419,867 | 4/1947 | Woodman | 2/403 |
| 2,450,789 | 10/1948 | Frieman | 604/397 |
| 2,508,811 | 5/1950 | Best | 604/392 |
| 2,548,162 | 4/1951 | Karels | 604/386 |
| 2,570,963 | 10/1951 | Mesmer | 604/392 |
| 2,583,553 | 1/1952 | Faure | 604/397 |
| 2,627,859 | 2/1953 | Hargrave | 604/394 |
| 2,638,899 | 5/1953 | Ambarian | 604/397 |
| 2,657,689 | 11/1953 | Kay | 604/398 |
| 2,671,220 | 3/1954 | Geissmann | 2/111 |
| 2,688,328 | 9/1954 | Marcus | 604/397 |
| 2,691,376 | 10/1954 | Tunmell | 604/386 |
| 2,779,077 | 1/1957 | Kline | 441/64 |
| 2,798,489 | 7/1957 | Behrman | 604/399 |
| 2,833,282 | 5/1958 | Moore | 604/386 |
| 2,890,700 | 6/1959 | Lonberg-Holm | 604/364 |
| 2,898,912 | 8/1959 | Adams | 604/397 |
| 2,910,982 | 11/1959 | Woodward | 604/392 |
| 2,931,361 | 4/1960 | Sostrin | 604/392 |
| 3,397,406 | 8/1968 | Leach | 2/111 |
| 3,452,753 | 7/1969 | Sanford | 604/401 |
| 3,707,969 | 1/1973 | Sanford | 604/347 |
| 3,756,878 | 9/1973 | Willot | 604/358 |
| 4,470,411 | 9/1984 | Hoyt, Jr. | 128/165 |

FOREIGN PATENT DOCUMENTS

| 564424 | 2/1958 | Belgium | 2/406 |
|---|---|---|---|
| 0351204 | 2/1961 | Switzerland | 441/64 |
| 0493819 | 10/1938 | United Kingdom | 604/397 |
| 1377541 | 12/1974 | United Kingdom . | |
| 1414599 | 11/1975 | United Kingdom . | |

Primary Examiner—C. Fred Rosenbaum
Assistant Examiner—Sharon Rose
Attorney, Agent, or Firm—Francis J. Bouda

[57] ABSTRACT

A stretchable, knitted, panty-type holder for disposable or reuseable absorbent wound dressings or pads for babies or adults has a generally hour-glass shape with a back waistband portion and front waistband portion. The front waistband portion has at least one opening formed in each end thereof, and the back waistband portion has at least one ribbed or enlarged portion formed near the ends thereof. When applied to the body of a patient with an absorbent pad placed therein, the back waistband portion, which has a free end extending beyond the enlargements therein, is brought around the waist and passed through the opening in the adjacent end of the front waistband portion until the enlargement is secured adjacent the opening, whereupon the free end of the back waistband portion is tucked inside the holder between the body of the patient and the inside of the holder.

9 Claims, 1 Drawing Sheet

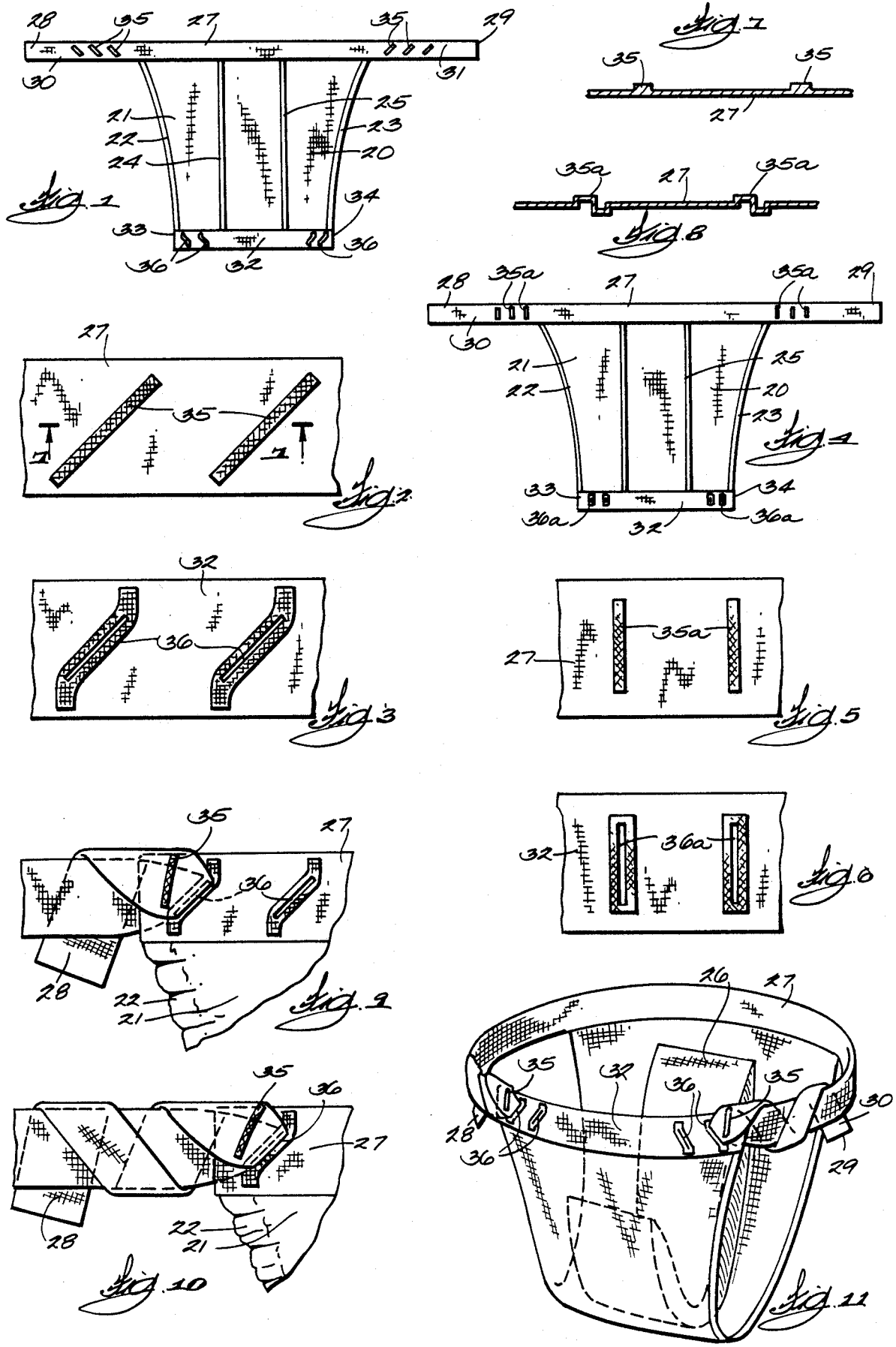

PAD HOLDER

The present invention relates to a garment generally described as a pad holder or pant used with an absorbent pad for holding body exudates as in baby diapers, adult incontinence pads, etc.

Baby diapers and adult diapers are not new, and in the United States the most popular version is the one-piece plastic-backed diaper illustrated by the Buell U.S. Pat. No. 3,860,003 for baby diapers and in Strickland U.S. Pat. No. 4,253,461 and for adult diapers.

Many years before the development of the one-piece diaper the two-piece system was well-known in Europe as well as in the United States, and generally included an undergarment (which could be wrapped around the patient or baby), inside of which an absorbent cloth or washable or reusable absorbent pad was placed.

An early version of this type of diaper shown in the Bewsic U.S. Pat. No. 971,659 and many others such as Earnshaw U.S. Pat. No. 1,079,479, Alsop U.S. Pat. No. 1,977,604, Frieman U.S. Pat. No. 2,450,789, Best U.S. Pat. No. 2,508,811, Faure U.S. Pat. No. 2,583,553, Kay U.S. Pat. No. 2,657,689, Marcus U.S. Pat. No. 2,688,328, and Behrman U.S. Pat. No. 2,798,489.

However, most of the early devices were constructed and arranged to be tied around the torso of the patient (with the absorbent pad inside). As can be seen from the patents, the arrangement was complicated and difficult to apply to the patient, particularly if the baby was a squirming, wriggling infant, or if the adult patient was senile, mentally unbalanced, or mentally deficient.

Improvement in this type of garment came with the development of the "snap-fasteners", and these are illustrated in the patents of Woodman U.S. Pat. No. 2,419,867, Sanford U.S. Pat. No. 3,452,753 and Sanford U.S. Pat. No. 3,707,969.

These last-mentioned garments are more convenient in their operation and application, but are more expensive because of the use of the "snap-fasteners". In some cases "snap-fasteners" were replaced with buttons and buttonholes, which were more difficult to operate than the "snap-fasteners", but both arrangements were generally more convenient than the tie-mechanism of the early devices.

A unique hook-like arrangement holder is described in the Lonberg-Holm U.S. Pat. No. 2,890,700, but this construction provided a stiff, uncomfortable, and undesirable waistband.

The more recent and more popular devices are the tape-tab fasteners shown in the Buell U.S. Pat. No. 3,848,594 and the Schaar U.S. Pat. No. 4,378,800. These are the devices generally used in commercial products at the present time.

Other designers have also suggested the use of hook and loop fasteners sold under the trademark "VELCRO", and in Scandinavia the tie-on plastic "SNIBB" is popular.

Several devices, including an apertured waistband, are shown in the Adams U.S. Pat. No. 2,898,912, the British Pat. No. 1414599, and the British Pat. No. 1377541, but like the many early patents, these devices also required an arrangement for tying the pad-holder about the torso of the user.

SUMMARY OF THE INVENTION

The side-opening self-securing mesh pad holder of the present invention overcomes the deficiencies of the early art as well as the present devices by providing an open-net, open-weave, breathable, inexpensively manufactured pad-holder which can be applied easily to the patient and which will hold an absorbent pad securely in place without the use of buttons, hooks, snap-fasteners, hook and loop fasteners, tie mechanism, or the like.

Moreover, the pad holder of the present invention can be inexpensively and easily manufactured on knitting machines which incorporate in the product elastic threads which bring the pad-holder closely around and against the torso of the user.

The pad-holder of the present invention has a basic design which is a modified hour-glass shape constructed of open knit or open-weave fabric having a greater density of horizontal fibers in a waistband. The waistband is ribbed in the back portion and slotted in the front to allow for securing, by a single tuck around the waistband, the device in place on a non-ambulatory patient or, with a double tuck, on an ambulatory patient.

This device eliminates knots or bulges which exist in the other devices, and thus avoids abrasion of the skin. Additionally, the breathable characteristic of the fabric allows air to pass through the holder for greater comfort, and helps to avoid skin rash, tissue trauma, or the like. Furthermore, the device provides a means by which the care-giver or nurse can easily examine the patient, and it eliminates patient discomfort during the removal of the garment for examination.

With the above and other objects in view, more information and a better understanding of the present invention may be achieved by reference to the following detailed description.

DETAILED DESCRIPTION

For the purpose of illustrating the invention, there is shown in the accompanying drawings a form thereof which is at present preferred, although it is to be understood that the instrumentalities of which the invention consists can be variously arranged and organized and that the invention is not limited to the precise arrangements and organizations of the instrumentalities as herein shown and described.

In the drawings, wherein like reference characters indicate like parts:

FIG. 1 is a plan view of one embodiment of the holder of the present invention, stretched out and laid flat.

FIG. 2 is an enlarged portion of the back tab end of the waistband portion of the device of FIG. 1.

FIG. 3 is an enlarged view of the front waistband portion of the device of FIG. 1.

FIG. 4 is a view similar to FIG. 1 of a modified embodiment of the present invention.

FIG. 5 is a view similar to FIG. 2 showing the back tab-end portion of the embodiment illustrated in FIG. 4.

FIG. 6, similar to FIG. 3, illustrates the front waistband portion of the embodiment of FIG. 4.

FIG. 7 is a cross-sectional view taken generally along line 7—7 of FIG. 2.

FIG. 8 is a modification of the ribbed waistband portion shown in FIG. 7.

FIG. 9 illustrates the single-tuck fastening arrangement for non-ambulatory patients.

FIG. 10 illustrates a double-tuck fastening arrangement for ambulatory patients.

FIG. 11 is a perspective view illustrating how the pad holder of the present invention appears when wrapped around the torso of the patient and with an absorbent pad disposed therein.

In FIG. 1, pad-holder 20 of the present invention includes an open-knit or open-weave fabric 21 which can be formed on a Raschel-type knitting machine of the type described in U.S. Pat. Nos. 3,656,323, 3,656,324 and 3,899,900. The fabric 21 generally includes a plurality of elastic ribs 22 and 23 defining curved edge-portions creating a modified hour-glass shape or tulip-shaped product, as shown in FIG. 1.

Additional elastic-rib portions 24 and 25 may be formed in the body portion 21 which aid in securing the absorbent pad 26 in place when the holder is applied to the torso of a patient.

A back waistband portion 27 has relatively longer end-portions 28 and 29 extending laterally therefrom to create a pair of tabs 30 and 31 which can be wrapped around the patient as shown particularly in FIG. 11.

The front waistband portion 32 is somewhat shorter than the back waistband portion 27 and may, desirably, terminate in the end portions 33 and 34 which are disposed substantially at the front of the patient when the pad-holder is in position on the body as shown in FIG. 11.

In the tabs 30 and 31, a plurality of ribs 35 is knitted so as to create enlargements in the cross-section thereof, as is shown in FIG. 7. These ribs 35 create abutments or enlargements in the tabs 30 and 31 for the purposes to be hereinafter described.

In the front waistband portions 33 and 34, a plurality of slots or openings 36 is created through which the tabs 30 and 31 may pass, as is also shown in FIG. 11.

In the preferred form of my invention shown in FIG. 2, the ribs 35 are disposed at an angle which may be, but not limited to, approximately 45 degrees.

Similarly the slots 36, formed like "buttonholes" in the waistband portions 33 and 34, are disposed at a similar angle, as is shown in FIG. 3.

In FIGS. 4, 5, and 6 there is shown a modification of my invention wherein the ribs 35a and the slots 36a are disposed generally at a right angle to the tabs 30 and 31.

The ribbing illustrated in FIG. 8 is a modification of that shown in FIG. 7 and is adapted to provide a structure wherein the enlargements extend on both sides of the tabs 30 and 31 so as to increase the frictional resistance or to provide greater impediment to the passage of the tabs 30 and 31 through the slots 36.

As is shown in FIGS. 2 and 5, there is a plurality of the ribs, and as illustrated in FIGS. 3 and 6, there is a plurality of slots, and this provides for a greater selection on the part of the patient or care-giver for adjustment of the holder around the torso and waistline of the patient.

As can be seen particularly in FIGS. 9, 10, and 11, the tabs 30 and 31 are drawn through the slots 36 from the inner-side of the waistband portions 33 and 34 until the ribs 35 come into engagement with the slots 36. Thereafter the free end of the tabs 30 and 31 are pulled rearwardly around the patient and upwardly over the waistband and tucked behind the waistband-portion created by the portions of the tabs 30 and 31 more nearly adjacent the body portion of the waistband 27. This is clearly shown in FIG. 11 and further illustrated in FIGS. 9 and 10.

In FIG. 9, a single tuck is made with only one looping of the tab around the waistband before it is tucked between the holder and the body of the patient (inside the holder). This is generally sufficient for a non-ambulatory patient.

However, the arrangement shown in FIGS. 10 and 11 includes a double-tuck wherein the tabs 30 and 31 make a double-loop around the secured portions of the tabs 30 and 31 to provide a more secure anchoring arrangement for ambulatory patients. This is clearly shown in FIG. 11.

It is obvious from the foregoing that there is no need for buttons, snaps, pins, hooks, adhesive tabs, hook and loop fasteners or the like, and the fixation of the holder in place around the body of a baby or an adult can be done easily by one person, using one hand, and without the need for any tying or other difficult fastening means.

The elimination of snaps, buttons, pins, and tape reduces the cost of the garment and provides a device which can be adjusted properly to fit several sizes of patients and provides greater comfort, air permeability, and cosmetic appearance than the devices of the prior art. The holder can be made rapidly and inexpensively on well-known knitting machines, thereby to keep the cost of manufacture as low as possible.

It is to be understood that the present invention may be embodied in other specific forms without departing from the spirit or special attributes hereof, and it is therefore desired that the present embodiments be considered in all respects as illustrative, and therefore not restrictive, reference being made to the appended claims rather than to the foregoing description to indicate the scope of the invention.

Having thus described my invention, what I claim as new and desire to protect by Letters Patent are the following:

1. A side-opening, breathable, flexible, adjustable, self-securing holder for absorbent pads, for babies or adults, said holder being generally hour-glass shaped and formed of a mesh material and including
   a body portion
   a flexible and adjustable front waistband portion attached to a first end of said body portion
   a back waistband portion attached to a second end of said body portion and interlocking with said first waistband portion
   said front waistband portion being shorter in length than said back waistband portion
   at least one rib-reinforced opening formed in each end of said front waistband portion
   at least one rib with adjacent indention in each end of said back waistband portion constructed of width sufficient to interlock with the said rib reinforced opening of said front waistband portion, when said back waistband portion is inserted through said openings, and
   a portion of said back waistband, at each end, extending outwardly beyond the said rib with adjacent indentions.

2. A holder of claim 1 wherein said breathable material is knitted with an open-mesh pattern.

3. A holder of claim 1 wherein said breathable material is woven with an open-mesh pattern.

4. A holder of claim 1 wherein said body has a plurality of elastic strands therein.

5. A holder of claim 1 wherein the openings in the front waistband portion are buttonhole-like openings.

6. A holder of claim 1 wherein the ribs in the back waistband portion are formed in the back waistband member by increasing the thickness of the material thereof.

7. A holder of claim 1 wherein two or more rib-reinforced openings are formed in the front waistband portion at each end thereof, and two or more ribs with adjacent indentations are formed in the back waistband portion adjacent each end thereof.

8. A holder of claim 1 wherein the ribs at each end of the back waistband portion protrude only on one side of the waistband.

9. A holder of claim 1 wherein the ribs at each end of the back waistband portion protrude on both sides of the said waistband portion.

* * * * *